US012789011B2

(12) United States Patent
Brown

(10) Patent No.: US 12,789,011 B2
(45) Date of Patent: Nov. 10, 2026

(54) TREATMENT TECHNIQUE FOR CARDIAC TARGETS

(71) Applicant: Elekta Limited, Crawley (GB)

(72) Inventor: Kevin John Brown, Crawley (GB)

(73) Assignee: Elekta Limited, Crawley (GB)

( * ) Notice: Subject to any disclaimer, the term of this patent is extended or adjusted under 35 U.S.C. 154(b) by 370 days.

(21) Appl. No.: 17/904,045

(22) PCT Filed: Feb. 22, 2021

(86) PCT No.: PCT/EP2021/054342
§ 371 (c)(1),
(2) Date: Aug. 11, 2022

(87) PCT Pub. No.: WO2021/165540
PCT Pub. Date: Aug. 26, 2021

(65) Prior Publication Data

US 2023/0085445 A1 Mar. 16, 2023

(30) Foreign Application Priority Data

Feb. 20, 2020 (GB) ..................................... 2002361

(51) Int. Cl.
*A61N 5/10* (2006.01)

(52) U.S. Cl.
CPC ......... *A61N 5/1068* (2013.01); *A61N 5/1045* (2013.01); *A61N 5/1049* (2013.01); (Continued)

(58) Field of Classification Search
CPC .. A61N 5/1068; A61N 5/1045; A61N 5/1049; A61N 5/1067; A61N 2005/1055; A61N 2005/1089
See application file for complete search history.

(56) References Cited

U.S. PATENT DOCUMENTS

| | | | |
|---|---|---|---|
| 8,295,435 | B2 | 10/2012 | Wang et al. |
| 2008/0177280 | A1 | 7/2008 | Adler et al. |

(Continued)

FOREIGN PATENT DOCUMENTS

| | | |
|---|---|---|
| CN | 109219469 | 1/2019 |
| EP | 3456383 | 3/2021 |
| WO | 2020107121 | 6/2020 |

OTHER PUBLICATIONS

"International Application Serial No. PCT/EP2021/054342, International Search Report dated May 20, 2021", (May 20, 2021), 4 pgs.

(Continued)

*Primary Examiner* — Patricia J Park
(74) *Attorney, Agent, or Firm* — Schwegman Lundberg & Woessner, P.A.

(57) ABSTRACT

A radiotherapy device is disclosed. The radiotherapy device includes a radiation source, a detecting means and controller communicatively coupled to the radiation source and the detecting means. The radiation source is configured to generate a treatment beam for irradiating a subject. The detecting means is configured to detect a motion of the subject, the motion comprising a first physiological motion component and a second physiological motion component. The controller is configured to generate a beam shaping control signal based on the first physiological motion component and to generate a beam gating control signal based on the second physiological motion component

23 Claims, 7 Drawing Sheets

(52) U.S. Cl.
CPC .... *A61N 5/1067* (2013.01); *A61N 2005/1055* (2013.01); *A61N 2005/1089* (2013.01)

(56) References Cited

U.S. PATENT DOCUMENTS

| | | | | |
|---|---|---|---|---|
| 2009/0180589 | A1 | 7/2009 | Wang et al. | |
| 2012/0083645 | A1 | 4/2012 | Sun et al. | |
| 2013/0109904 | A1 | 5/2013 | Siljamaeki et al. | |
| 2016/0074674 | A1* | 3/2016 | Kohli | A61B 5/0531 600/484 |
| 2018/0280734 | A1* | 10/2018 | Clayton | A61N 5/1083 |
| 2019/0038919 | A1 | 2/2019 | Lachaine | |
| 2019/0388708 | A1* | 12/2019 | Kumar | A61N 5/1031 |
| 2021/0370097 | A1* | 12/2021 | Thomas | A61N 5/1081 |
| 2022/0386987 | A1* | 12/2022 | Camps | A61B 5/0205 |

OTHER PUBLICATIONS

"International Application Serial No. PCT/EP2021/054342, Written Opinion dated May 20, 2021", (May 20, 2021), 6 pgs.
"United Kingdom Application Serial No. 20002361.0, Examination Report dated Jul. 16, 2020", (Jul. 16, 2020), 6 pgs.
"CN Application 2021800277116 First Office Action with Search Report", with English translation, 18 pages.
"EP20210707932 EPO Communication pursuant to Rule 114(2) EPC mailed Jul. 25, 2024", 3 pages.
"Chinese Application No. 202180027711.6, Office Action dated Jul. 4, 2025", w English Translation, (Jul. 4, 2025), 9 pgs.
"European Application No. 25196841.8, Search Report dated Nov. 3, 2025", Nov. 3, 2025, 6 pgs.
"Chinese Application No. 202180027711.6, Office Action dated Nov. 10, 2025", w English Translation, Nov. 10, 2025, 19 pgs.

* cited by examiner

TREATMENT TECHNIQUE FOR CARDIAC TARGETS

PRIORITY APPLICATIONS

This application is a U.S. National Stage Filing under 35 U.S.C. § 371 from International Application No. PCT/EP2021/054342, filed on Feb. 22, 2021, and published as WO2021/165540 on Aug. 26, 2021, which claims the benefit of priority to United Kingdom Application No. 2002361.0, filed on Feb. 20, 2020; the benefit of priority of each of which is hereby claimed herein, and which applications and publication are hereby incorporated herein by reference in their entireties.

This disclosure relates to radiotherapy devices, and in particular to controlling radiotherapy devices for irradiating cardiac targets.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc. The radiotherapy device can be used to apply radiation to a tumour. In addition, the radiotherapy device can be used for non-tumour applications, for example to apply radiation to create a lesion in the heart to treat a pre-existing condition.

In radiotherapy treatment, it is desirable to deliver a prescribed dose of radiation to a target region of a subject and to limit irradiation of other parts of the subject, i.e. to healthy tissue. Motion of the subject can cause a decreased dose to be applied to the target region and/or an increased dose to be applied to the healthy tissue. To address this, known techniques include monitoring a location and/or movement of the subject and gating the treatment beam such that radiation is applied only when the subject (i.e. the target region within the subject) is in a desired location and not when the subject/target region is in a suboptimal location. Other known techniques include shaping a beam of radiation using a collimator, such as a multi-leaf collimator. This enables a cross-sectional shape of the treatment beam to be adapted to a particular shape of a tumour. By movement of the collimator or parts thereof, it is also possible to adapt the shape of the treatment beam based on the location and/or movement of the subject.

There are various physiological motions that can contribute to a total motion of a subject. Gross or large-scale movements of a subject may include shifting position, coughing or sneezing. The subject may also undergo cyclical, physiological movement. For example, the subject may undergo respiratory motion due to their breathing cycle and may undergo cardiac motion based on beating of their heart. These pseudo-periodic motions are generally asynchronous. Typically, the motions have different frequencies and are temporally offset. The respiratory motion is generally relatively slow, comprising approximately 12 to 20 breaths per minute. In contrast, the cardiac motion is generally relatively fast, comprising approximately 60-100 beats per minute.

It may be difficult or impossible to shape a beam using a collimator quickly enough to account for or react to the cardiac motion. Further, the cardiac motion and the respiratory motion are superimposed to create a complex total motion of the subject. This total motion may lead to the tumour being in a desired location at irregular intervals, for only a small fraction of a treatment time and/or for only brief time durations. It is not desirable to gate the beam when either cardiac motion or respiratory motion cause the target region to be in a suboptimal location, since this would lead to gating of the beam for a large fraction of the total treatment time. Irradiating simultaneously in both a defined respiratory phase and a defined cardiac phase would therefore lead to infrequent irradiation and implausibly long treatment times. Therefore, it can be difficult to control a treatment beam accurately and efficiently to account for complex physiological motions.

These considerations are of particular importance when the target region is at or near the heart, i.e. for cardiac targets. For such targets, the cardiac motion (and to some degree the respiratory motion) is more likely to affect whether the target region is aligned with the region that is actually irradiated by the treatment beam. For safety reasons, it is important not to irradiate unintended locations in or around the heart.

Stereotactic body radiation therapy (SBRT) can be used to irradiate precisely-defined target regions with high doses of radiation. These treatments may be particularly suitable for irradiation of small target regions located close to an organ at risk, e.g. for cardiac targets. Further, there is interest in using SBRT for treating atrial fibrillation, which causes an irregular and/or abnormally fast heart rate. SBRT can be used to ablate part of the heart tissue and thereby treat atrial fibrillation. High spatial and temporal precision is required for such techniques and physiological motions must be accounted for in order to avoid irradiating unintended locations within the subject.

It would be advantageous to provide improved means for accounting for and reacting to patient motions during radiotherapy treatment. In addition, it would be advantageous to provide more dynamic and responsive beam delivery. Accordingly, there is a need for more accurate and efficient control of a treatment beam to account for physiological motions.

The present invention seeks to address these and other disadvantages encountered in the prior art.

SUMMARY

An invention is set out in the independent claims.

According to an aspect, there is provided a radiotherapy device. The radiotherapy device comprises a radiation source, detecting means and a controller communicatively coupled to the radiation source and the detecting means. The radiation source is configured to generate a treatment beam for irradiating a subject. The detecting means is configured to detect a motion of the subject. The motion comprises a first physiological motion component and a second physiological motion component. The controller is configured to generate a beam shaping control signal based on the first physiological motion component and a beam gating control signal based on the second physiological motion component.

According to a further aspect, there is provided a computer-implemented method for generating control signals for a radiotherapy device. The computer-implemented method comprises detecting a motion of a subject, generating a beam shaping control signal and generating a beam gating control signal. The motion comprises a first physiological motion component and a second physiological motion component. The beam shaping control signal is generated based on the first physiological motion component. The beam gating control signal is generated based on the second physiological motion component.

According to a further aspect, there is provided a computer-readable medium comprising computer-executable instructions. The computer-executable instructions, when executed by a processor, cause the processor to perform the method described above.

FIGURES

Specific embodiments are now described, by way of example only, with reference to the drawings, in which.

Figure 2:
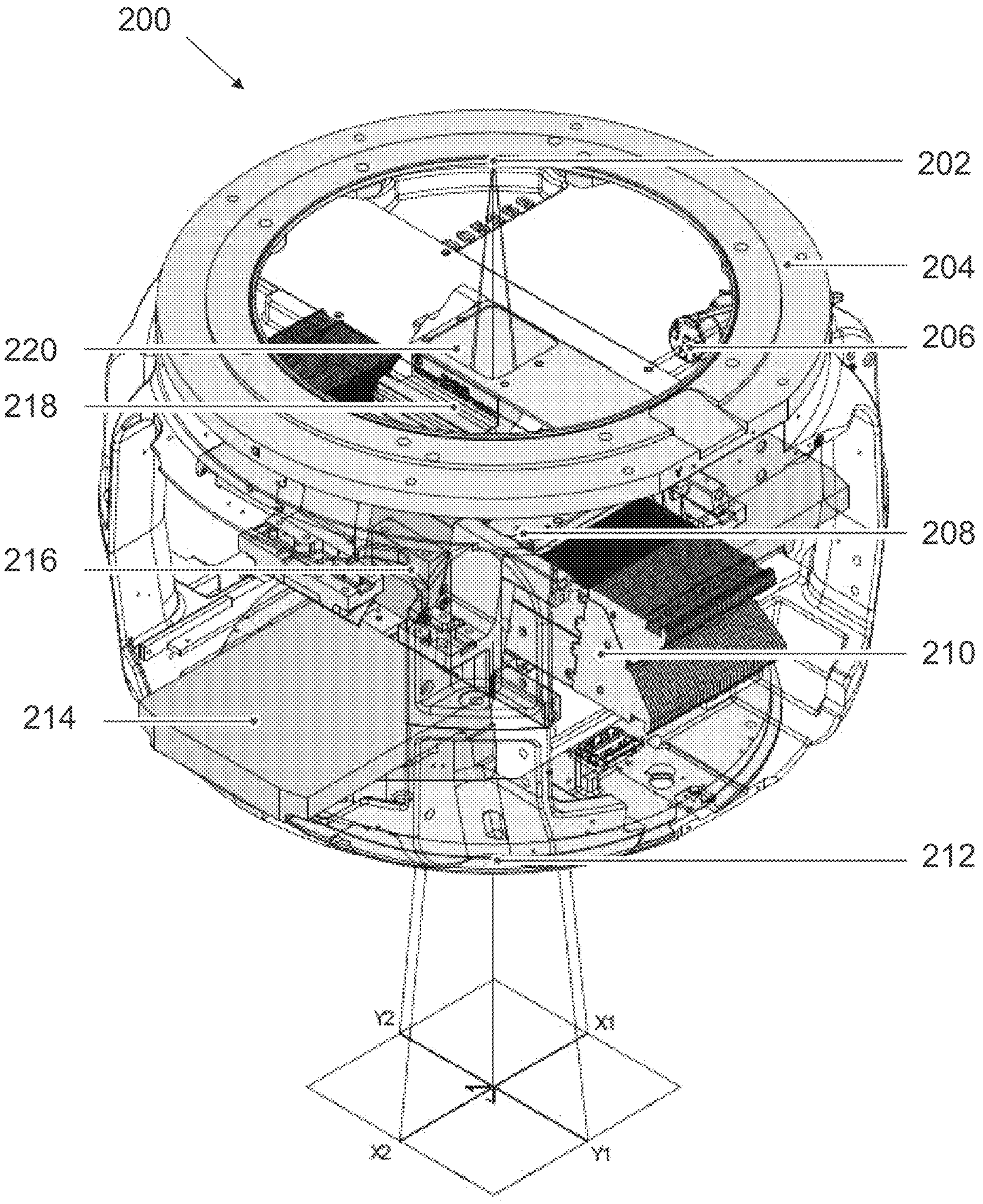
FIG. 2 depicts a beam limiting device comprising a multi-leaf collimator and diaphragm apparatus.
Figure 3A:
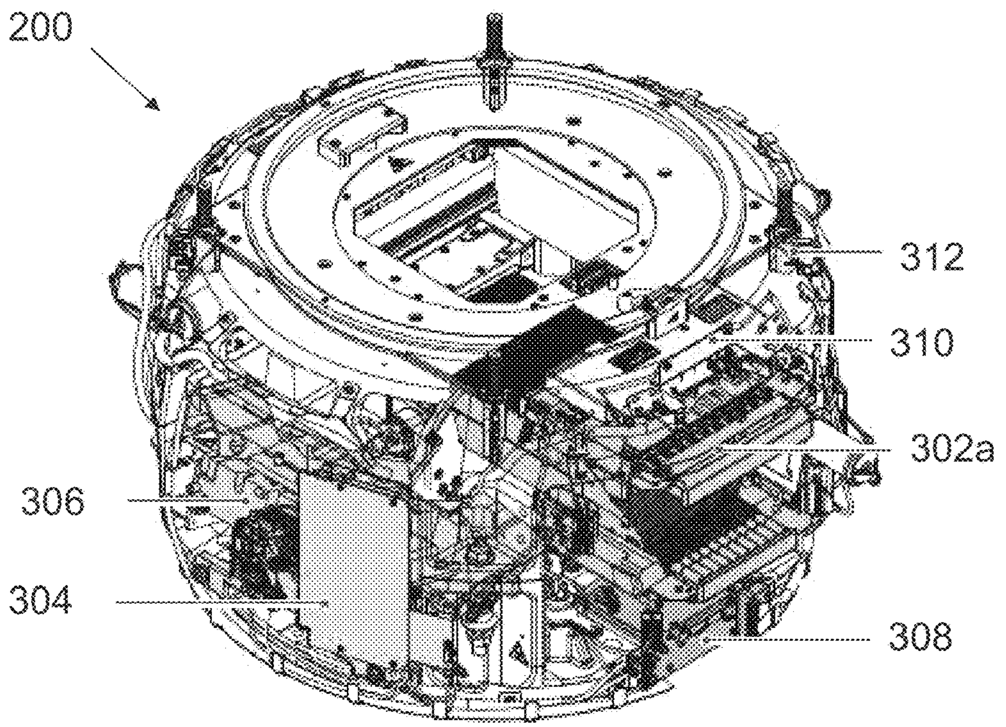
Figure 3B:
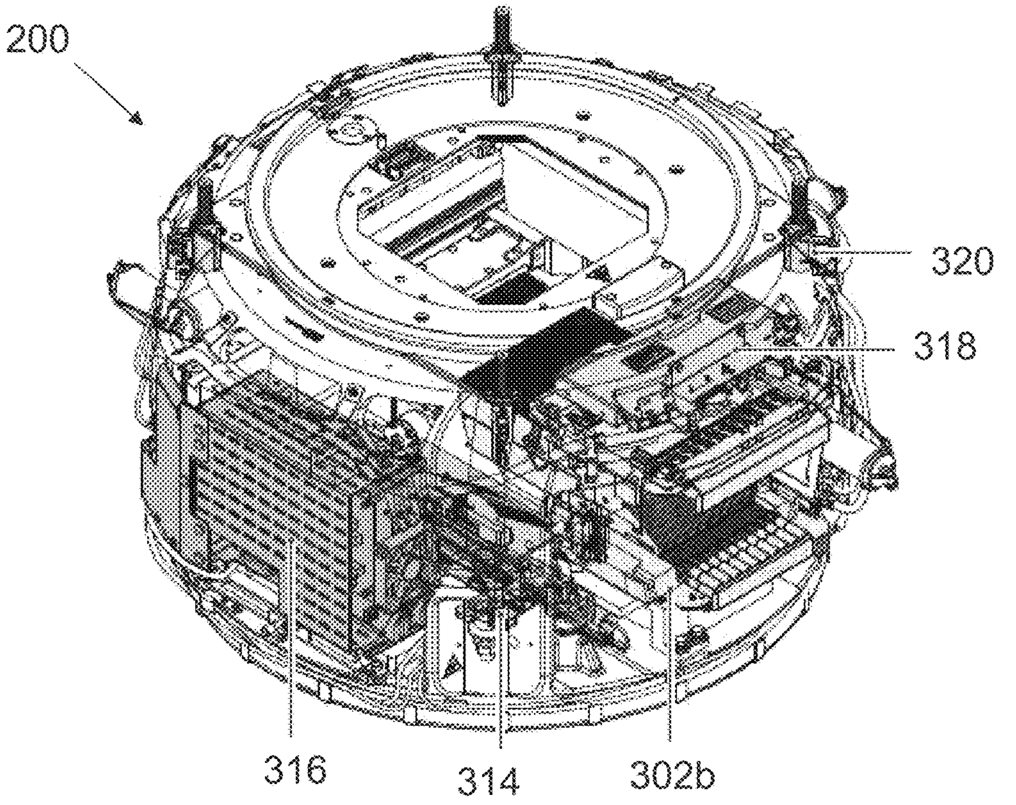
Figure 4:
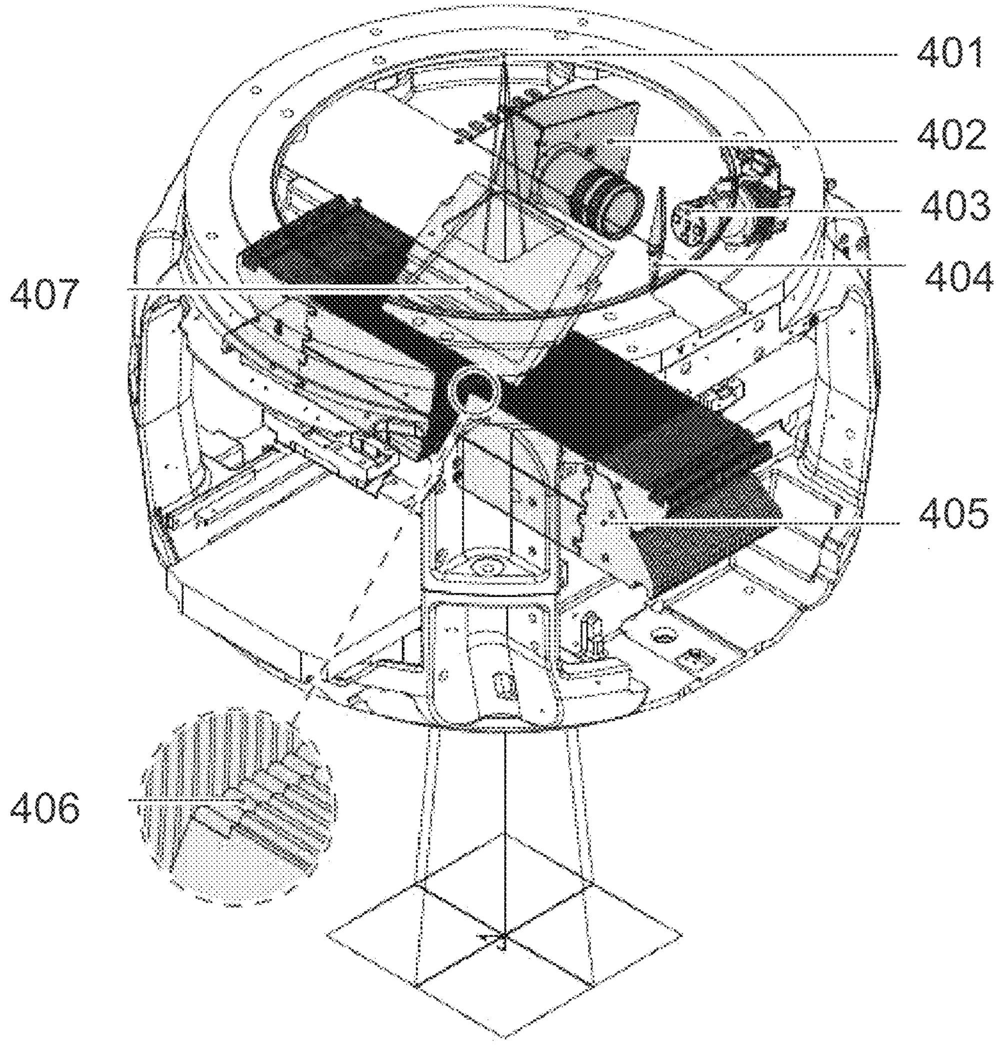
Figure 5:
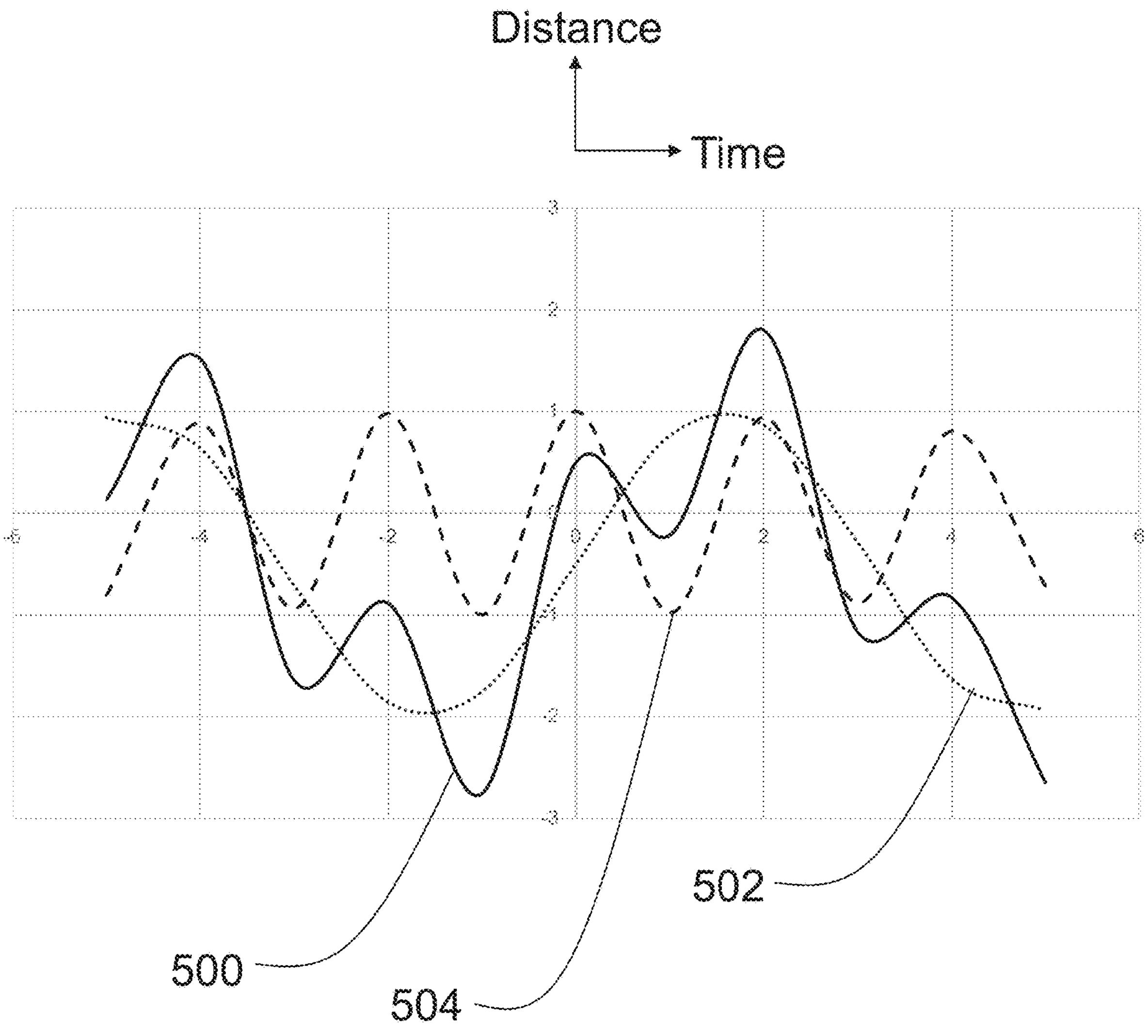
Figure 6:
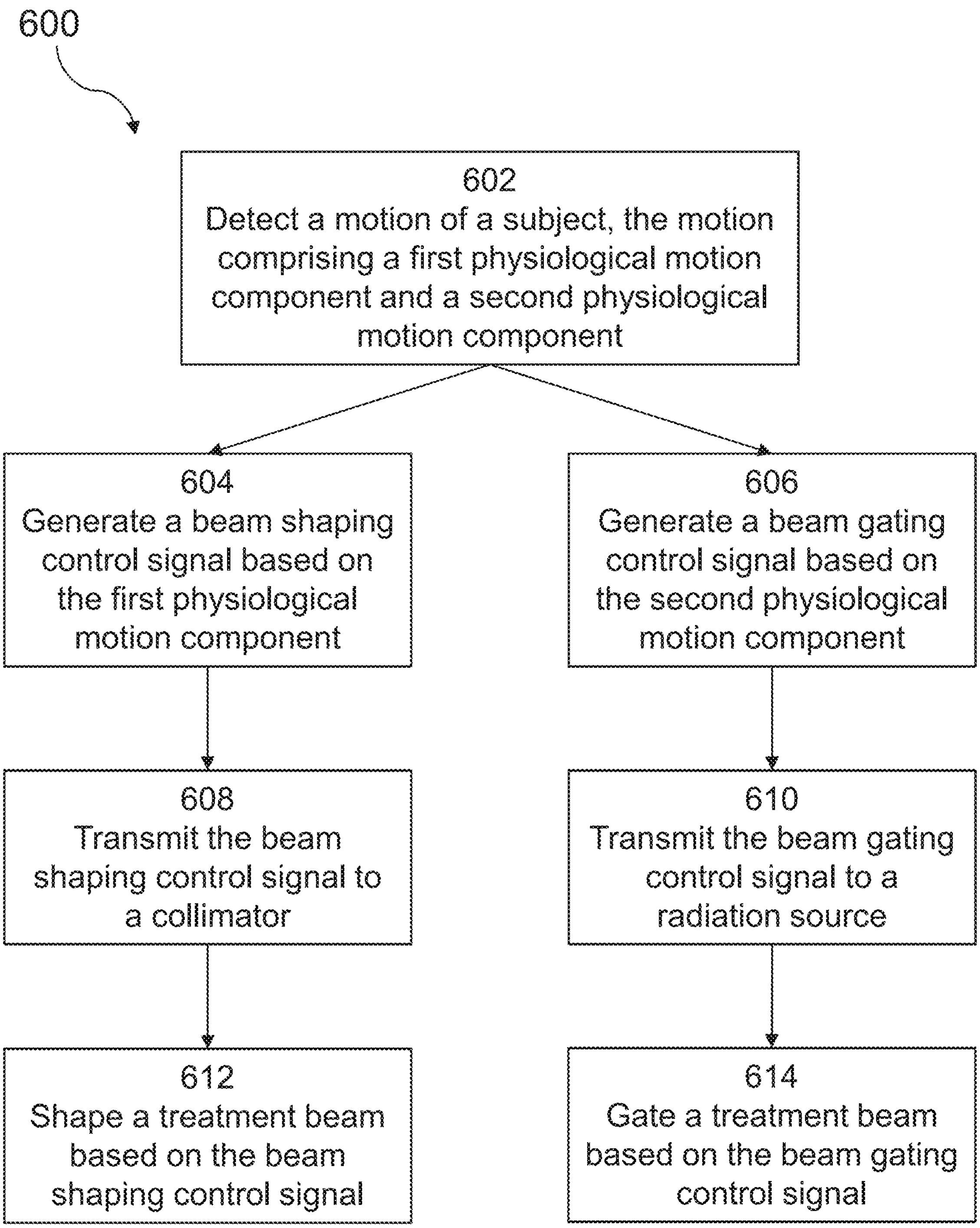

FIGS. 3*a* and 3*b* depict the beam limiting device of FIG. 2 but at different angles and with different components highlighted;

FIG. 4 depicts a beam limiting device comprising a position determining apparatus;

FIG. 5 depicts motion of a subject or a target region according to the present disclosure;

FIG. 6 depicts a method for controlling a radiotherapy device according to the present disclosure.

Figure 7:
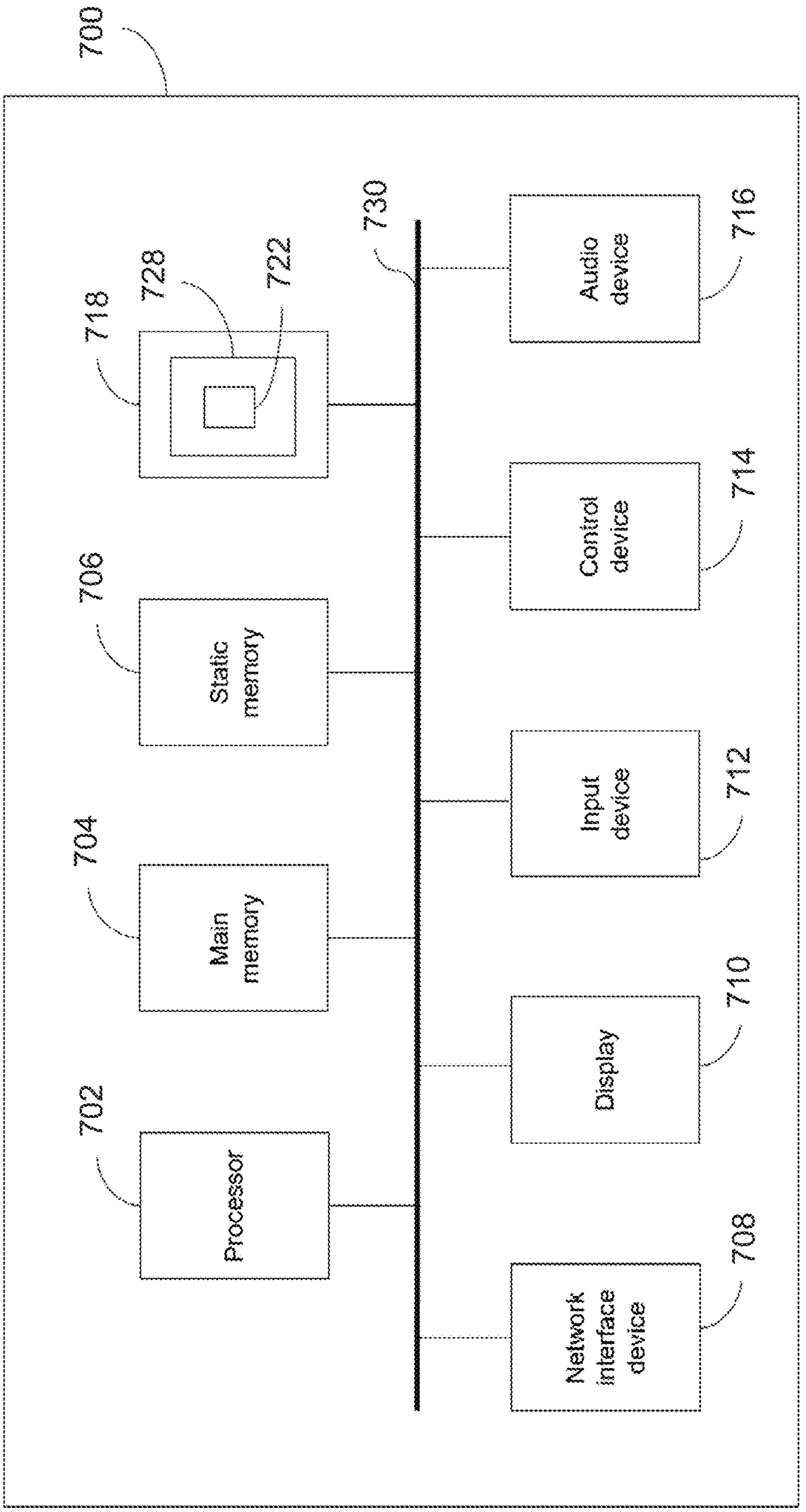

FIG. 7 depicts a block diagram of a computing device configured to perform one or more of the methods described herein.

DETAILED DESCRIPTION

The present disclosure relates to control of a radiotherapy device. It is desirable to only apply radiation to a target region of a subject when the target region is in an optimal position. However, the motion of the target region may be complex, including components relating to different physiological processes such as breathing of the subject and beating of the subject's heart. It may not be possible to shape a treatment beam to account for the fluctuations in the total motion and it may not be desirable to gate the treatment beam to account for the fluctuations in the total motion as this may lead to infrequent application of radiation and long treatment times. To address this, a controller of the radiotherapy device may generate and transmit a beam shaping control signal based on a first physiological motion component of the target region and generate and transmit a beam gating control signal based on the second physiological motion component of the target region. In this manner, the total motion is accounted for and reacted to in a dynamic, accurate and efficient way.

Figure 1:
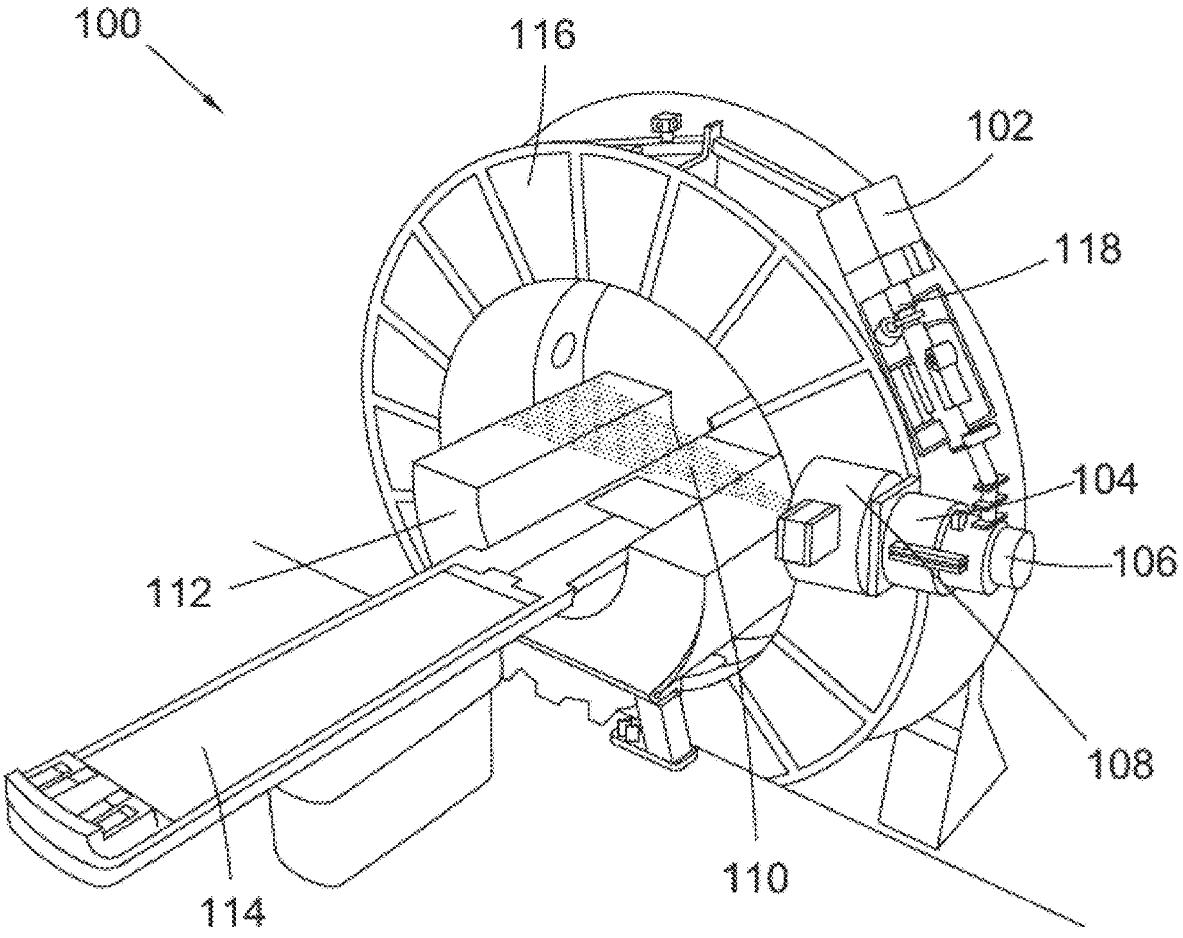
FIG. 1 depicts a radiotherapy device or a radiotherapy apparatus.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device 100 depicted in FIG. 1 is an MR-linac. The device 100 comprises both MR (magnetic resonance) imaging apparatus 112 and radiotherapy (RT) apparatus which may comprise a linac device. The MR imaging apparatus 112 is shown in cross-section in the diagram. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons 106, a source of radiation, a collimator 108 such as a multi-leaf collimator configured to collimate and shape the beam, MR imaging apparatus 112, and a patient support surface 114. In use, the device would also comprise a housing (not shown) which, together with the ring-shaped gantry, defines a bore. The moveable support surface 114 can be used to move a patient, or other subject, into the bore when an MR scan and/or when radiotherapy is to commence. The MR imaging apparatus 112, RT apparatus, and a subject support surface actuator are communicatively coupled to a controller or processor. The controller is also communicatively coupled to a memory device comprising computer-executable instructions which may be executed by the controller.

The radiation source may comprise a beam generation system. For a linac, the beam generation system may comprise a source of RF energy 102, an electron gun 106, and a waveguide 104. The radiation source is attached to the rotatable gantry 116 so as to rotate with the gantry 116. In this way, the radiation source is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 106, such as an electron gun 106, is also coupled to the waveguide 104 and is configured to inject electrons into the waveguide 104. In the electron gun 106, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. The electrons travel toward a heavy metal target which may comprise, for example, tungsten. Whilst the electrons travel through the flight tube, an arrangement of focusing magnets act to direct and focus the beam on the target.

The source of radiation is configured to direct a beam 110 of therapeutic radiation toward a patient positioned on the patient support surface 114. When the electrons strike the target, X-rays are produced in a variety of directions. A primary collimator may block X-rays travelling in certain directions and pass only forward travelling X-rays to produce a treatment beam 110. The beam can be shaped in various ways by a beam-limiting device or beam-shaping apparatus, for example by using a multi-leaf collimator 108, before it passes into the patient as part of radiotherapy treatment.

In some implementations, the source of radiation is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface 114. The controller is communicatively coupled to a memory, e.g. a computer readable medium.

The linac device also comprises several other components and systems as will be understood by the skilled person. For example, in order to ensure the linac does not leak radiation, appropriate shielding is also provided.

The apparatus may be configured to perform any of the method steps presently disclosed and may comprise computer executable instructions which, when executed by a processor, cause a processor to perform any of the method steps presently disclosed. Any of the steps that the apparatus is configured to perform may be considered as method steps of the present disclosure and may be embodied in computer executable instructions for execution by a processor.

In a radiotherapy apparatus the beam can be delimited using a beam limiting device such as a multi-leaf collimator (MLC). This is a collimator which consists of a large number of elongate thin leaves arranged side to side in an array. The leaves may be made from a high atomic numbered material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator can comprise two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam. The components and operation of an example of such a device will be described generally for the purpose of providing useful accompanying information for the present invention.

FIG. 2 depicts an example of a beam limiting device (BLD) 200. FIG. 2 schematically depicts the position of a target 202, from which X-rays are produced, and schematically shows the beam passing through the BLD 200. The BLD 200 comprises an interface ring 204 configured to allow the BLD to be attached to other components of the treatment head, for example an ion chamber and/or dosimeter. The BLD 200 also comprises a source of light 206 such as a projector which forms part of an optical detection system which has the purpose of detecting the location of each of the leaves of the MLC, including those forming part of the leaf bank 210 shown in FIG. 2. As will be better appreciated upon inspection of FIGS. 3*a* and 3*b*, the BLD 200 comprises two banks of leaves which face each other across the radiation field. Each bank comprises a plurality of leaves. For example, in a particular implementation each bank comprises 80 leaves. The BLD may also comprise one or more of an accessory ring 212, side shielding 216, a wedge 218 and a shutter 220.

The MLC comprises a dynamic leaf guide (DLG). The dynamic leaf guide comprises a leaf bank support, leaf bank actuation means, and guide means. The leaf banks are each supported on a respective leaf bank support. Each leaf bank support is configured and structured so as to provide support for the entire bank of leaves. The leaf bank actuation means is configured to move the entire bank of leaves such that the bank of leaves may be extended into, and withdrawn from, the radiation field. The leaf bank actuation means is configured to move the leaf bank support along guide means. The guide means may be referred to as a leaf bank guide, and may comprise a guide rail or ridge. The leaf bank actuation means, which may be described as a leaf bank guide motor or DLG motor, is configured to extend the leaf bank along the leaf bank guide into the path of a radiation beam. In other words, each DLG is configured such that, upon actuation of the DLG motor, each leaf in the leaf bank is moved by an equal amount into, or out from, the path of the beam in a direction defined by the guide. Additionally, the MLC may comprise a guide brake configured to halt the movement of the leaf bank along the guide when the bank has reached the required position.

In addition to movement of the leaf bank via the DLG, each leaf is individually actuatable, for example by a suitable arrangement of lead screws and leaf actuators/leaf motors. The MLC comprises leaf actuation means by which each individual leaf can be independently extended into, and withdrawn from, the radiation field. The leaf actuation means may comprise leaf motors and an arrangement of lead screws. Various arrangements for providing actuation of the leaves of MLCs are known to the skilled person and will not be discussed in detail herein. During treatment, when the MLC collimates the beam to form a particular beam shape, for example in accordance with a treatment plan, the DLGs move the leaf banks forward into the radiation field. Once the banks are in the correct position, each leaf is individually actuated so as to form the desired shape. In other words, the MLC presents an edge to the radiation beam which can be varied so as to provide a particular beam shape.

FIGS. 3*a* and 3*b* depict the beam limiting device 200 of FIG. 2, with different internal components highlighted. FIG. 3*b* shows the BLD rotated through an angle of roughly 180 degrees from the view depicted in FIG. 3*a* so that both sides of the BLD can be seen. Beam limiting device 200 comprises a first leaf bank 302*a*, which can be better seen in FIG. 3*a*, and a second leaf bank 302*b*, which can be better seen in FIG. 3*b*. In terminology used by the applicant, the first leaf bank 302*a* may be described as a Y1 leaf bank 302*a* and the second leaf bank 302*b* may be described as a Y2 leaf bank.

The BLD 200 comprises a DLG PCB cage 304 configured to hold a DLG PCB in place. The DLG PCB may be described as a drive PCB. The drive PCB is configured to control movement of the leaf guide e.g. via the guide motor. The drive PCB may therefore hold a microprocessor and circuitry configured to receive and action control signals received from a separate control means. An optics assembly 306 forms part of the optical detection system which allows the movement of each of the leaves to be tracked. The BLD 200 comprises a plurality of PCBs, including a signal and power PCB 308 which controls signals received by and sent to the BLD and also the power provided to each component, an accessory PCB 310, a diaphragm PCB 318, and a router, CCU, wedge and LED PCB which is held by cage 316. The PCBs are each configured to control operation of the components to which they are connected in a known manner. The BLD 200 also comprises a touchguard actuator 320, which forms part of a touchguard system which is configured to detect if the treatment head is in close proximity to the patient or another object so as to avoid collision.

A further component of the BLD 200 and/or the MLC is a leaf position monitoring and/or detection system. Such a system is depicted in FIG. 4 within the BLD. It is desirable to monitor the actual position of the leaves of the MLC in order to provide feedback and allow their position to be adjusted accurately. Such systems may be based on optical vision technology and/or the use of fluorescent markers. The skilled person will be aware of such systems, however for completeness a short description is provided below.

The leaf position monitoring system may comprise the source of light 403 (206 in FIG. 2) such as an LED projector, a light detector 402 such as a camera, and one or more reflective markers 406 positioned on each leaf of the MLC. FIG. 4 shows two banks of leaves, with one being labelled 405. The light detector 402 is configured and positioned to 'view' the reflective leaf markers 406. The system may also comprise reference markers which are not placed on an MLC leaf but which may be placed, for example, at particular positions within the field of view such as at the corners of the field of view. By shining light on the MLC leaves using the source of light 402, light is reflected from optical markers 406 on the MLC leaves and detected at the detector 402. Light is also reflected form the reference markers, which is also detected at the detector. Signals received at the detector may be processed in a known way to determine the position of each of the MLC leaves. The optical detection system may comprise a number of mirrors 407 in order to allow illumination of the MLC leaves and to direct reflected light to the detector.

The MLC leaf position monitoring system may alternatively, or additionally, make use of fluorescent markers placed on each MLC leaf. These markers may also be described as optical markers 406. Again with reference to FIG. 4, a suitable fluorescent marker may be comprised of ruby. In an example implementation, ruby markers 406 may be illuminated by a source of light 402 (e.g. a 410 nm monochromatic source). This source of light 402 may be, for example, an LED. The LED may be configured to emit light in the UV range, in particular if the fluorescent markers 406 on the leaves are rubies. This will cause the ruby marker to fluoresce, emitting light in a variety of directions and onto a dichroic beamsplitter 404 which diverts a proportion of the light to a camera 402 protected by an infrared pass filter. This IR pass filter will limit the light incident on the camera to that emitted by the fluorescent ruby markers 406. By using reference markers in the same manner as described above it is possible to determine the position of each of the fluorescent markers and hence determine the position of each of the MLC leaves. In a particular implementation, ultraviolet light from an LED source produces infrared fluorescence when it falls on the ruby tips 406 of the multi-leaf collimator leaves. This infrared fluorescence, detected by an infrared camera 402, is used to reliably monitor and accurately position the leaves and can be viewed in real time on the linear accelerator's display screen.

More generally, the radiotherapy device/apparatus may comprise a multi-leaf collimator, and a position determining apparatus which is configured to determine the position of one or more leaves of a multi-leaf collimator. Each of the one or more leaves comprises an optical marker. The position determining device comprises a source of illumination configured to illuminate the one or more leaves, and a light detection means, configured to detect light received from the optical markers. The source of illumination may be referred to as a light source. While reference is made to 'optical' and 'light', it will be understood that the system is not limited to use of illumination in the visible part of the spectrum. The optical marker is configured to reflect the illumination and/or fluoresce at the wavelength of illumination.

The beam limiting apparatus of the device also comprises a diaphragm apparatus. The diaphragm apparatus is configured to shape the beam of radiation, in a manner similar to the MLC. The diaphragm apparatus comprises one or more diaphragms 214 (also known as 'jaws') configured to be extended into, and withdrawn from, the radiation field. In an example, the diaphragm apparatus comprises two diaphragms 214 which face each other across the radiation field. The diaphragm apparatus further comprises diaphragm actuation means, for example a diaphragm motor, which is configured to effect this movement. The diaphragms may be configured to move in a movement axis which is generally or substantially perpendicular to the beam axis, and also generally or substantially perpendicular to the movement axis of the MLC leaves.

With reference to FIG. 2, it will be appreciated that the actuation means of the MLC is configured to move the MLC leaves 210 in the directions indicated as Y1 and Y2, and along a movement axis depicted in the figure as the 'Y' direction. The diaphragm apparatus is configured to move the diaphragms in directions X1 and X2, and along a movement axis depicted in the figure as the 'X' direction. While the diaphragm 214 depicted in FIG. 2 is positioned 'underneath' the MLC (i.e. farther away from the beam source 202), in alternative implementations the diaphragm may be positioned 'above' the MLC (i.e. closer to the beam source 202 than the MLC). It is advantageous for diaphragms 214 to be configured to move orthogonally to the MLC leaves 210 to improve the ability of the collimator to define the edge of the radiation field, for example to enable application of radiation with a desired spatial profile.

The diaphragm apparatus further comprises a control means, such as a PCB. The apparatus further comprises a current sensing means configured to provide a signal indicative of current supplied to the diaphragm actuation means. This may be a current sensor such as an ammeter. The current sensing means may form part of the control means and may be for example positioned on the PCB. The control means and current sensor may be similar in type to the other control means and current sensors described herein. The current sensor is communicatively coupled with a controller of the radiotherapy device. The positions of the MLC leaves 210 and the diaphragms 214 may be controlled by the same controller or control of the positions of the MLC leaves 210 and control of the positions of the diaphragms 214 may be performed by different, integrated controllers. It is advantageous for the control of the MLC leaves 210 and the diaphragms 214 to be integrated to enable dynamic control of the collimation of the beam.

A beam shaping control signal as described herein may comprise instructions for moving one or more of the leaves of the MLC and/or for moving one or more of the leaf banks of the MLC and/or for moving one or more of the diaphragms of the MLC. The beam shaping control signal may comprise instructions for effecting such movements immediately, at a defined later time, after a defined interval, or some combination of these. The beam shaping control signal may therefore comprise instructions for time-varying or time-dependent shaping of the beam by the MLC. In other words, the beam shaping control signal may comprise a plurality of instructions for shaping the beam based on the motion of the subject and/or the location of the target region (e.g. a tumour). The motion may comprise a first physiological motion component, for example a respiratory motion.

It will be understood that other collimators, for example other multi-leaf collimators, and other arrangements for driving collimators or multi-leaf collimators can be used in combination with the systems and methods of the present disclosure.

Gating of the treatment beam of the radiotherapy device will now be described. It will be understood that application of radiation by the radiation source in some time periods but not in others may be achieved by selectively gating the treatment beam emitted by the radiation source. The radiation source may comprise a particle source, for example an electron source 106 and a radiofrequency (RF) field source 102 (as shown in FIG. 1). The electron source may provide a source of electrons which generate a radiation dose to be delivered to the subject, for example by impacting a target. The RF field source may electromagnetically accelerate the electrons to a desired velocity suitable for providing the radiation dose. The radiation source may be gated by selectively controlling the electron source to be on (active) or off (inactive). Alternatively, or in addition, the radiation source 100 may be gated by selectively controlling the RF field source to be on (active) or off (inactive). In this manner, application of a radiation dose by the radiation source can be controlled according to desired parameters, for example based a beam gating control signal according to the present disclosure.

The radiation source may comprise a radiation source controller suitable for controlling the radiation source, for example by gating the radiation source or stopping gating of the radiation source. The controller may transmit the beam gating control signal to the radiation source controller. The beam shaping control signal may comprise instructions for effecting such gating or stopping such gating immediately, at a defined later time, after a defined interval, or some combination of these. The beam gating control signal may therefore comprise instructions for time-varying or time-dependent gating of the beam by the radiation source. In other words, the beam gating control signal may comprise a plurality of instructions for gating the beam based on the motion of the subject and the location of the target region (e.g. a tumour). The motion may comprise a second physiological motion component, for example a cardiac motion.

Detection of motion and/or a location of a target region and/or a subject may be performed using detecting means. As used herein, the detecting means may be described as a detector or a detecting apparatus. The detecting means may comprise the MR imaging apparatus 112 described in relation to FIG. 1. This MR imaging apparatus 112 may be configured to produce MR images of the subject and may comprise a primary magnet, one or more gradient coils, one or more receive coils, and an RF pulse applicator. The operation of the MR imaging apparatus may be controlled by the controller or by an MR imaging apparatus controller or by a combination of these. The MR imaging apparatus 112 may detect the motion and/or location of the subject before, during and/or after a radiotherapy treatment. In other words, the MR imaging apparatus 112 may be configured to provide time-dependent information on the motion and/or location of the subject. This may comprise information regarding the motion and/or location of the target region which it is intended to irradiate. Alternatively, or in addition, this may comprise information regarding the motion and/or location of an organ at risk, such as the heart of the subject. Therefore, the MR imaging apparatus 112 may be configured to provide information on the first physiological motion component, for example respiratory motion, and may be configured to provide information on the second physiological motion component, for example cardiac motion. It will be appreciated that other detecting means known to the skilled person could be used in place of or in combination with the MR imaging apparatus 112.

References to the detecting means as used herein may be used to refer to a single detecting means configured to determine a first physiological motion component and a second physiological motion component, or may be used to refer to a first detecting means configured to determine a first physiological motion component and a second detecting means configured to determine a second physiological motion component. The first detecting means may transmit a signal identifying the first physiological motion component to the controller. The second detecting means may transmit a signal identifying the second physiological motion component to the controller.

The first physiological motion component, for example the respiratory motion, may be detected by the MR imaging apparatus 112 (first detecting means). The second physiological motion component, for example the cardiac motion, may be detected by an external detecting means (second detecting means).

The external detecting means may comprise one or more known heart rate monitors. For example, the external detecting means may comprise an electrocardiographic (ECG) sensor. Such sensors measure the bio-potential generated by electrical signals that control the expansion and contraction of heart chambers. The sensor may be mounted on a chest strap to be worn by a subject. A transmitter mounted on the ECG sensor may transmit signals relating to the beating of the heart of the subject to a receiver coupled to the controller. Alternatively, or in addition, the external detecting means may comprise a photoplethysmographic (PPG) sensor. Such sensors use scattering of light from blood vessels of a subject to measure volumes of blood and thereby derive signals relating to the beating of the heart of the subject. A transmitter mounted on the PPG sensor may transmit signals relating to the beating of the heart of the subject to a receiver coupled to the controller.

The MR imaging apparatus 112 may determine the first physiological motion component, for example the respiratory motion, by sampling a spatial region of the subject that is weakly affected by the second physiological motion. For example, the MR imaging apparatus 112 may sample a region spatially separated from the heart. The treatment beam can be collimated using a beam shaping control signal based on the first physiological motion component. This avoids the need for the subject to hold their breath during the treatment in an attempt to prevent respiratory motion. The subject holding their breath may be uncomfortable for the subject, may not be adequate for eliminating all respiratory motion of the subject and/or may not be possible for long treatment times.

The MR imaging apparatus 112 may be configured to detect the first physiological motion component based on imaging a first spatial region of the subject and may be configured to detect the second physiological motion component based on imaging a second spatial region of the subject. The first spatial region may be weakly affected by the second physiological motion component. The second spatial region may be weakly affected by the first physiological motion component. In other words, the first and second physiological motion components may be measured based on different spatial locations to limit mixing of the first and second physiological motion components.

The detecting means may be communicatively coupled to a controller of the radiotherapy device. The controller may comprise, or be described as, a computing device or a processor. The controller may be any machine capable or executing a set of instructions (sequential or otherwise) that specify actions to be taken by the radiotherapy device and the components thereof as described herein. The controller may be communicatively coupled to some or all of the components of the radiotherapy device as described herein. In other words, the controller may be configured to receive information or instructions from one or more of these components and to transmit information or instructions to one or more of these components. In some examples, one or more controllers may be integrally formed with one or more of these components such that a separate controller is not needed.

The detecting means may transmit the motion and/or location information to the controller. The motion and/or location information may comprise a motion and/or location of a target region. The controller may analyse this information and may determine a first physiological motion component and a second physiological motion component therefrom.

The controller may comprise or have access to (i.e. be communicatively coupled to) a database containing known or expected patterns of subject motion. These may be derived from previous radiotherapy treatments and/or input by an operative. The expected patterns of motion may be defined generally for all subjects, may be specific to subjects with particular health metrics or physical parameters, or may be individually defined for a particular subject.

The controller may comprise one or more curve fitting algorithms for analysis of the motion. Respiratory motion typically causes pseudo-periodic motion, for example in the form of a sinusoid with a frequency in a given range and with an amplitude in a given range. The sinusoid has a particular phase depending on the point in the respiratory cycle the information is measured from. The sinusoid has a particular amplitude offset, i.e. may not have an average displacement of zero, depending on the location defined as corresponding to an amplitude of zero.

Cardiac motion typically causes pseudo-periodic motion. This may be described using a sinusoid with a frequency in a different given range and an amplitude in a different given range. The sinusoid has a particular phase depending on the point in the cardiac cycle the information is measured from. This may be different to the phase of the respiratory cycle. The sinusoid has a particular amplitude offset, i.e. may not have an average displacement of zero, depending on the location defined as corresponding to a displacement of zero. This may be different to the amplitude offset of the respiratory cycle.

Advantageously, the cardiac motion may alternatively be described by way of a signal comprising a baseline amplitude with periodic excursions from that baseline amplitude. These excursions may have a characteristic and measurable frequency, amplitude, phase, amplitude offset and profile. The profile, describing the shape of the excursions when represented on an amplitude-time graph, may be pre-defined in the database. The profile may be defined generally for all subjects, may be specific to subjects with particular health metrics or physical parameters, or may be individually defined for a particular subject. This may enable more accurate and efficient parameterisation of the cardiac motion. It is advantageous to deliver radiation during the baseline periods of the cardiac motion and to gate the radiation during the excursions in order to ensure accurate delivery of the radiation to the intended region of the subject.

Discrete motion of a subject such as due to coughing or sneezing typically causes an abrupt, discrete motion with a relatively large amplitude in a further given range.

These patterns of motion may be described using equations stored in the database. The equations may have variable parameters for quantities such as frequency, amplitude, phase and amplitude offset which the controller can perform an optimisation or curve fitting to determine, as would be understood by a person skilled in the art. While sinusoids are referred to above, it will be understood that any suitable equations can be defined and used to describe the patterns of motion. For example, more complex equations may be defined for describing the respiratory and/or cardiac motion more accurately.

In examples for which a single detecting means is used, the controller is configured to distinguish between these components of motion, and to determine that the motion comprises two or more identifiable motion components. For example, the controller may use the optimisation process described above to determine that the total motion can be described as a superposition of two motions, each described using one of the equations described above, and each corresponding to a physiological motion of the subject. One or more of these motions may be pseudo-periodic. In other words, one or more of the motions may be approximately periodic, i.e. may be periodic to a predefined level of accuracy. In other words, one or more of the motions may only differ from periodic motion within a predefined threshold. The superposition may not describe the motion exactly. Instead, there may also a further, for example a random, component of the motion which is not described by the superposition. Using this analysis, the controller may determine the first and second components of the total motion, i.e. may determine the first and second physiological motion components. One or more of the first and second physiological motion components may correspond to respiratory motion or cardiac motion.

FIG. 5 depicts motion of a subject or a target region according to the present disclosure. It will be appreciated that the motion has been simplified for ease of understanding. A real motion signal may vary in a more irregular way. The x-axis represents time and the y-axis represents distance, i.e. amplitude of motion. The scales depicted on the distance and time axes are representative and should not be understood as limiting the present disclosure. In an example, the x-axis may be in units of seconds and the y-axis may be in units of centimetres. The information received by the controller from the detecting means may correspond to the total motion 500 (solid line). As will be appreciated, this is a complex signal describing a complex pattern of motion. The motion comprises a first motion component 502 (dotted line) and a second motion component 504 (dashed line). In other words, the total motion 500 is the sum or superposition of the first motion component 502 and the second motion component 504. The first motion component 502 may represent a first physiological motion component, for example a respiratory motion. The second motion component 504 may represent a second physiological motion component, for example a cardiac motion.

The first motion component 502 and the second motion component 504 will in general, but not necessarily, have one or more of different frequencies, different amplitudes, different phases and different amplitude offsets. In examples for which a single detecting means is used, these may be identified by the controller using curve fitting/optimisation as described above. One or more of these parameters may change over time. The detecting means may continue to provide the motion information during a treatment such that the controller can continually, or at intervals, update the optimisation during the treatment. The controller may use the pseudo-periodicity of one or more of the motions to predict future motion and may provide control signals for a certain time period in the future, for example for the next second or tenth of a second. Gating may be used as a safety backstop in the event that the subject or the target region is detected as deviating from this predicted motion.

It may be desirable to only apply radiation to a target region/subject when the target region/subject is in an optimal position (optionally within a threshold). It will be appreciated that the total motion 500 describes a complex pattern. It may not be possible to timely shape the treatment beam, for example using an MLC, to account for all of the fluctuations in the total motion 500. It may not be desirable to gate the treatment beam, for example using the radiation source 112, to account for all of the fluctuations in the total motion 500 as this may lead to infrequent application of radiation and long treatment times. Previous approaches in the field have stressed the benefits of using gating, or stressed the benefits of using dynamic beam shaping. In other words, previous approaches have argued why one of these techniques should be used instead of the other.

In contrast, according to the present disclosure, the controller may generate and transmit a beam shaping control signal based on the first motion component 502 and may generate and transmit a beam gating control signal based on the second motion component 504. The beam can thereby be gated during periods when the cardiac motion causes the target region to be in a suboptimal location and the beam shape or direction can be adjusted by the collimator during periods when the respiratory motion causes the target region to be in a suboptimal location. This change in the beam shape or direction can enable the irradiation to continue by providing that the target region and an irradiated region continue to coincide during the respiratory motion. In this manner, the total motion 500 can be accounted for and reacted to in a dynamic, accurate and efficient way.

FIG. 6 depicts a method 600 for controlling a radiotherapy device according to the present disclosure. The method may be a computer-implemented method.

In a step 602, a motion of a subject may be detected. The motion may be detected using a detecting means. The detecting means may comprise a single detecting means or first and second detecting means as described above. For example, the detecting means may comprise an MR imaging apparatus 112, an external detecting means, or other imaging means communicatively coupled to a controller. The motion comprises a first physiological motion component and a second physiological motion component. One or both of the first physiological motion component and the second physiological motion component may comprise a periodic or pseudo-periodic component. In some examples, the first physiological motion component may comprise a respiratory motion of the subject. In some examples, the second physiological motion component may comprise a cardiac motion of the subject. In examples for which a single detecting means is used, the first physiological motion component and the second physiological motion component may be determined from the detected motion using the optimisation process described in relation to FIG. 5.

In a step 604, a beam shaping control signal may be generated based on the first physiological motion component. The beam shaping control signal may be generated by the controller. The beam shaping control signal may comprise an instruction to collimate a treatment beam and/or an instruction not to collimate a treatment beam. The beam shaping control signal may comprise instructions to collimate the treatment beam during a first time period and/or not to collimate the treatment beam during a second time period. The beam shaping control signal may comprise instructions to collimate the treatment beam to cause the treatment beam to have a first shape in a first time period and/or to collimate the treatment beam to cause the treatment beam to have a second shape in a second time period. The collimator may comprise a multi-leaf collimator as described herein. The beam shaping control signal may comprise instructions to cause individual leaves and/or groups of leaves of the multi-leaf collimator to move to shape the treatment beam to form a desired shape. Alternatively, or in addition, the beam shaping control signal may comprise instructions to cause one or more diaphragms to move to shape the beam to form a desired shape.

In a step 606, a beam gating control signal may be generated based on the second physiological motion component. The beam gating control signal may be generated by the controller. The beam gating control signal may comprise an instruction to gate the treatment beam and/or an instruction to stop gating the treatment beam. The beam gating control signal may comprise instructions to gate the treatment beam during a first time period and/or not to gate the treatment beam during a second time period.

The steps 602, 604 and 606 may comprise a method for generating control signals for a radiotherapy device. This method may be a computer-implemented method.

In a step 608, the beam shaping control signal may be transmitted to a collimator. The beam shaping control signal may be transmitted by the controller, which may be communicatively coupled to the collimator. The collimator may be a multi-leaf collimator.

In a step 610, the beam gating control signal may be transmitted to a radiation source. The radiation source may be communicatively coupled to the controller.

In a step 612, the treatment beam may be shaped based on the beam shaping control signal. The treatment beam may be shaped using the collimator, for example the multi-leaf collimator, which may shape the treatment beam according to the instructions in the beam shaping control signal.

In a step 614, the treatment beam may be gated based on the beam gating control signal. The treatment beam may be gated using the radiation source, which may gate the treatment beam according to the instructions in the beam gating control signal. The radiation source may gate the treatment beam by selectively controlling a particle source, for example an electron source, to be on or off. Alternatively, or in addition, the radiation source may gate the treatment beam by selectively controlling an RF field source to be on or off.

One or more of steps 604, 608 and 612 may overlap in time with one or more of steps 606, 610 and 614. This may depend on the particular motion of the subject/target region. For example, steps 604 and 606 may occur at the same time or at approximately the same time. Steps 608 and 610 may occur at the same time or at approximately the same time. Steps 612 and 614 may occur at the same time or at approximately the same time.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

FIG. 7 illustrates a block diagram of one implementation of a computing device 700 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a secondary memory (e.g., a data storage device 718), which communicate with each other via a bus 730.

Processing device 702 represents one or more general-purpose processors such as a microprocessor, central processing unit, or the like. More particularly, the processing device 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. Processing device 702 is configured to execute the processing logic (instructions 722) for performing the operations and steps discussed herein.

The computing device 700 may further include a network interface device 708. The computing device 700 also may include a video display unit 710 (e.g., a liquid crystal display (LCD) or a cathode ray tube (CRT)), an alphanumeric input device 712 (e.g., a keyboard or touchscreen), a cursor control device 714 (e.g., a mouse or touchscreen), and an audio device 716 (e.g., a speaker).

The data storage device 718 may include one or more machine-readable storage media (or more specifically one or more non-transitory computer-readable storage media) 728 on which is stored one or more sets of instructions 722 embodying any one or more of the methodologies or functions described herein. The instructions 722 may also reside, completely or at least partially, within the main memory 704 and/or within the processing device 702 during execution thereof by the computer system 700, the main memory 704 and the processing device 702 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A “hardware component” is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase “hardware component” should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as “receiving”, “determining”, “comparing”, “enabling”, “maintaining,” “identifying,” “applying,” “transmitting,” “generating,” or the like, refer to the actions and processes of a computer system, or similar electronic computing device, that manipulates and transforms data represented as physical (electronic) quantities within the computer system’s registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term “computer-readable medium” as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive.

Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The disclosure comprises the following clauses:

1. A radiotherapy device comprising:

a radiation source configured to generate a treatment beam for irradiating a subject;

detecting means configured to detect a motion of the subject, the motion comprising a first physiological motion component and a second physiological motion component; and a controller communicatively coupled to the radiation source and the detecting means, wherein the controller is configured to generate a beam shaping control signal based on the first physiological motion component and to generate a beam gating control signal based on the second physiological motion component.

2. A radiotherapy device according to clause 1, wherein the first physiological motion component comprises a first pseudo-periodic component.

3. A radiotherapy device according to clause 1 or clause 2, wherein the first physiological motion component comprises a respiratory motion.

4. A radiotherapy device according to any preceding clause, wherein the second physiological motion component comprises a second pseudo-periodic component.

5. A radiotherapy device according to any preceding clause, wherein the second physiological motion component comprises a cardiac motion.

6. A radiotherapy device according to any preceding clause, wherein the detecting means comprises:

a first detector configured to detect the first physiological motion component; and a second detector configured to detect the second physiological motion component.

7. A radiotherapy device according to any of clauses 1-5, wherein the detecting means comprises a detector configured to detect both the first physiological motion component and the second physiological motion component.

8. A radiotherapy device according to any preceding clause, wherein:

the radiotherapy device comprises a collimator communicatively coupled to the controller;

the controller is configured to transmit the beam shaping control signal to the collimator; and the collimator is configured to shape the treatment beam based on the beam shaping control signal.

9. A radiotherapy device according to any preceding clause, wherein:

the controller is configured to transmit the beam gating control signal to the radiation source; and the radiation source is configured to gate the treatment beam based on the beam gating control signal.

10. A radiotherapy device according to any preceding clause, wherein the detecting means comprises an MR imaging apparatus.

11. A radiotherapy device according to any preceding clause, wherein the beam shaping control signal and/or the beam gating control signal comprise time-varying instructions.

12. A radiotherapy device according to any preceding clause, wherein the radiotherapy device is configured to irradiate a cardiac target with the treatment beam.

13. A computer-implemented method for generating control signals for a radiotherapy device, the computer-implemented method comprising:

detecting a motion of a subject, the motion comprising a first physiological motion component and a second physiological motion component;

generating a beam shaping control signal based on the first physiological motion component; and generating a beam gating control signal based on the second physiological motion component.

14. A computer-implemented method according to clause 13, wherein the first physiological motion component comprises a first pseudo-periodic component.

15. A computer-implemented method according to clause 13 or clause 14, wherein the first physiological motion component comprises a respiratory motion.

16. A computer-implemented method according to any of clauses 13-15, wherein the second physiological motion component comprises a second pseudo-periodic component.

17. A computer-implemented method according to any of clauses 13-16, wherein the second physiological motion component comprises a cardiac motion.

18. A computer-implemented method according to any of clauses 13-17, wherein the detecting the motion of the subject comprises:

detecting the first physiological motion component using a first detector; and detecting the second physiological motion component using a second detector.

19. A computer-implemented method according to any of clauses 13-17, wherein the detecting the motion of the subject comprises using a detector to detect both the first physiological motion component and the second physiological motion component.

20. A computer-implemented method according to any of clauses 13-19, further comprising: transmitting the beam shaping control signal to a collimator.

21. A computer-implemented method according to any of clauses 13-20, further comprising: transmitting the beam gating control signal to a radiation source.

22. A computer-implemented method according to any of clauses 13-21, wherein the detecting the motion of the subject is performed using an MR imaging apparatus.

23. A computer-implemented method according to any of clauses 13-22, wherein the beam shaping control signal and/or the beam gating control signal comprise time-varying instructions.

24. A computer-implemented method according to any of clauses 13-23, wherein the beam shaping control signal and/or the beam gating control signal are for controlling irradiation of a cardiac target with a treatment beam.

25. A computer-readable medium comprising computer-executable instructions which, when executed by a processor, cause the processor to perform the method of any of clauses 13-24.

The invention claimed is:

1. A radiotherapy device comprising:

a radiation source configured to generate a treatment beam for irradiating a subject;

a motion detector, the motion detector configurable to detect a motion of the subject, the motion comprising a first physiological motion component representing a first physiological cycle and a second physiological motion component representing a different second physiological cycle; and a controller communicatively coupled to the radiation source and the motion detector, wherein the controller is configured to:

determine the first physiological motion component and the second physiological motion component from motion information received from the motion detector;

use a pseudo-periodicity of the first physiological motion component to predict a future motion of the first physiological motion component and to generate a first beam shaping control signal component based on the predicted future motion of the first physiological motion component; and use a pseudo-periodicity of the second physiological motion component to predict a future motion of the second physiological motion component and to generate a separate second beam gating control signal component based on the predicted future motion of the second physiological motion component, wherein the beam shaping control signal comprises a first plurality of instructions comprising time-varying instructions to collimate the treatment beam to cause the treatment beam to have a first shape in a first time period and to have a second shape in a second time period, based on the predicted future motion of the first physiological motion component, and wherein the beam gating control signal comprises a second plurality of instructions comprising time-varying instructions to gate the treatment beam during a third time period and not to gate the treatment beam during a fourth time period, based on the predicted future motion of the second physiological motion component, and wherein the beam shaping control signal and the beam gating control signal are generated at a same time or substantially the same time and together account for a total motion of the subject, the total motion comprising a superposition of the first physiological motion component and the second physiological motion component.

2. The radiotherapy device according to claim 1, wherein the first physiological motion component comprises a first pseudo-periodic component that approximates periodic motion to a predefined criterion.

3. The radiotherapy device according to claim 1, wherein the first physiological motion component comprises a respiratory motion.

4. The radiotherapy device according to claim 1, wherein the second physiological motion component comprises a second pseudo-periodic component that approximates periodic motion to a predefined criterion.

5. The radiotherapy device according to claim 1, wherein the second physiological motion component comprises a cardiac motion.

6. The radiotherapy device according to claim 1, wherein the motion detector comprises:

a first detector configured to detect the first physiological motion component; and a second detector configured to detect the second physiological motion component.

7. The radiotherapy device according to claim 1, wherein the motion detector comprises a detector configured to detect both the first physiological motion component and the second physiological motion component.

8. The radiotherapy device according to claim 1, wherein:

the radiotherapy device comprises a collimator communicatively coupled to the controller;

the controller is configured to transmit the first beam shaping control signal component to the collimator; and the collimator is configured to shape the treatment beam based on the first beam shaping control signal component.

9. The radiotherapy device according to claim 1, wherein:

the controller is configured to transmit the separate second beam gating control signal component to the radiation source; and the radiation source is configured to gate the treatment beam based on the separate second beam gating control signal component.

10. The radiotherapy device according to claim 1, wherein the motion detector comprises an MR imaging apparatus.

11. The radiotherapy device according to claim 1, wherein the radiotherapy device is configured to irradiate a cardiac target with the treatment beam.

12. A computer-implemented method for generating control signals for a radiotherapy device, the computer-implemented method comprising:

detecting, using a motion detector, a motion of a subject, the motion comprising a first physiological motion component representing a first physiological cycle and a second physiological motion component representing a different second physiological cycle, wherein the first physiological motion component and the second physiological motion component are determined from motion information received from the motion detector;

using a pseudo-periodicity of the first physiological motion component to predict a future motion of the first physiological motion component;

generating a first beam shaping control signal component based on the predicted future motion of the first physiological motion component;

using a pseudo-periodicity of the second physiological motion component to predict a future motion of the second physiological motion component; and generating a separate second beam gating control signal component based on the predicted future motion of the second physiological motion component, wherein the beam shaping control signal comprises a first plurality of instructions comprising time-varying instructions to collimate a treatment beam to cause the treatment beam to have a first shape in a first time period and to have a second shape in a second time period, based on the predicted future motion of the first physiological motion component, wherein the beam gating control signal comprises a second plurality of instructions comprising time-varying instructions to gate the treatment beam during a third time period and not to gate the treatment beam during a fourth time period, based on the predicted future motion of the second physiological motion component, and wherein the beam shaping control signal and the beam gating control signal are generated at a same time or substantially the same time and together account for a total motion of the subject, the total motion comprising a superposition of the first physiological motion component and the second physiological motion component.

13. The computer-implemented method according to claim 12, wherein the first physiological motion component comprises a first pseudo-periodic component.

14. The computer-implemented method according to claim 12, wherein the first physiological motion component comprises a respiratory motion.

15. The computer-implemented method according to claim 12, wherein the second physiological motion component comprises a second pseudo-periodic component.

16. The computer-implemented method according to claim 12, wherein the second physiological motion component comprises a cardiac motion.

17. The computer-implemented method according to claim 12, wherein the detecting the motion of the subject comprises:

detecting the first physiological motion component using a first detector; and detecting the second physiological motion component using a second detector.

18. The computer-implemented method according to claim 12, wherein the detecting the motion of the subject comprises using a detector to detect both the first physiological motion component and the second physiological motion component.

19. The computer-implemented method according to claim 12, further comprising:

transmitting the first beam shaping control signal component to a collimator; and transmitting the separate second beam gating control signal component to a radiation source.

20. The computer-implemented method according to claim 12, wherein the detecting the motion of the subject is performed using an MR imaging apparatus.

21. The computer-implemented method according to claim 12, wherein at least one of the first beam shaping control signal component or the separate second beam gating control signal component are for controlling irradiation of a cardiac target with a treatment beam.

22. A non-transitory computer-readable medium comprising computer-executable instructions which, when executed by a processor, cause the processor to perform operations, the operations comprising:

detecting, using a motion detector, a motion of a subject, the motion comprising a first physiological motion component representing a first physiological cycle and a second physiological motion component representing a different second physiological cycle, wherein the first physiological motion component and the second physiological motion component are determined from motion information received from the motion detector;

using a pseudo-periodicity of the first physiological motion component to predict a future motion of the first physiological motion component;

generating a first beam shaping control signal component based on the predicted future motion of the first physiological motion component;

using a pseudo-periodicity of the second physiological motion component to predict a future motion of the second physiological motion component; and generating a separate second beam gating control signal component based on the predicted future motion of the second physiological motion component, wherein the beam shaping control signal comprises a first plurality of instructions comprising time-varying instructions to collimate a treatment beam to cause the treatment beam to have a first shape in a first time period and to have a second shape in a second time period, based on the predicted future motion of the first physiological motion component, wherein the beam gating control signal comprises a second plurality of instructions comprising time-varying instructions to gate the treatment beam during a third time period and not to gate the treatment beam during a fourth time period, based on the predicted future motion of the second physiological motion component, and wherein the beam shaping control signal and the beam gating control signal are generated at a same time or substantially the same time and together account for a total motion of the subject, the total motion comprising a superposition of the first physiological motion component and the second physiological motion component.

23. The non-transitory computer-readable medium of claim 22, the operations further comprising:

transmitting the first beam shaping control signal component to a collimator; and transmitting the separate second beam gating control signal component to a radiation source.

* * * * *